(12) United States Patent
Guala

(10) Patent No.: US 9,889,287 B2
(45) Date of Patent: Feb. 13, 2018

(54) VALVE CONNECTOR FOR MEDICAL LINES

(75) Inventor: Gianni Guala, Turin (IT)

(73) Assignee: Industrie Borla S.p.A., Moncalieri (Turin) (IT)

( * ) Notice: Subject to any disclaimer, the term of this patent is extended or adjusted under 35 U.S.C. 154(b) by 1092 days.

(21) Appl. No.: 12/865,224

(22) PCT Filed: Jan. 23, 2009

(86) PCT No.: PCT/IB2009/000126
§ 371 (c)(1),
(2), (4) Date: Nov. 19, 2010

(87) PCT Pub. No.: WO2009/095760
PCT Pub. Date: Aug. 6, 2009

(65) Prior Publication Data
US 2011/0060293 A1    Mar. 10, 2011

(30) Foreign Application Priority Data
Jan. 29, 2008   (IT) .............................. TO2008A0059

(51) Int. Cl.
*A61M 39/10* (2006.01)
*A61M 39/26* (2006.01)

(52) U.S. Cl.
CPC ............ *A61M 39/10* (2013.01); *A61M 39/26* (2013.01); *A61M 2039/1033* (2013.01); *A61M 2039/1072* (2013.01)

(58) Field of Classification Search
CPC .......... A61M 39/10; A61M 2039/1033; A61M 2039/1072; A61M 39/22; A61M 39/26
(Continued)

(56) References Cited

U.S. PATENT DOCUMENTS

| 4,387,879 A | 6/1983 | Tauschiniski |
| 5,439,451 A | 8/1995 | Collinson et al. |
(Continued)

FOREIGN PATENT DOCUMENTS

| EP | 1747796 A1 | 1/2007 |
| EP | 1747796 B1 | 4/2008 |
(Continued)

OTHER PUBLICATIONS

PCT/ISA/210—International Search Report dated May 14, 2009, for corresponding PCT International Application No. PCT/IB2009/000126 filed Jan. 23, 2009.*
(Continued)

*Primary Examiner* — Shefali Patel
(74) *Attorney, Agent, or Firm* — Heslin Rothenberg Farley & Mesiti, PC; Victor Cardona, Esq.

(57) ABSTRACT

A valve connector for medical lines includes a tubular body having a male inlet fitting with an external luer cone, which can be coupled to a female tubular fitting with an internal luer cone, wherein the male inlet fitting includes an internally threaded external tubular element for screwed engagement with the female fitting, and an internal tubular element that can be displaced axially from a retracted position of closing to an advanced position of opening of a valve that controls a passage of flow through the connector. The internally threaded external tubular element is free to turn, and an arrangement is such that, when the internally threaded external tubular element is screwed off the female fitting and the passage of flow is closed by the valve, the external luer cone and the internal luer cone remain axially coupled to one another by friction.

11 Claims, 3 Drawing Sheets

(58) Field of Classification Search
USPC ........ 128/912; 604/513, 246, 248, 249, 256, 604/533, 534, 535, 537, 538, 539, 905
See application file for complete search history.

(56) References Cited

U.S. PATENT DOCUMENTS

| | | | |
|---|---|---|---|
| 5,676,346 A | 10/1997 | Leinsing | |
| 5,699,821 A | 12/1997 | Paradis | |
| 5,700,248 A | 12/1997 | Lopez | |
| 6,050,978 A | 4/2000 | Orr et al. | |
| 6,079,432 A | 6/2000 | Paradis | |
| 6,089,541 A | 7/2000 | Weinheimer et al. | |
| 6,206,861 B1 | 3/2001 | Mayer | |
| 6,299,132 B1 * | 10/2001 | Weinheimer | A61M 39/26 251/149.1 |
| 6,543,745 B1 | 4/2003 | Enerson | |
| 6,682,509 B2 | 1/2004 | Lopez | |
| 6,706,022 B1 | 3/2004 | Leinsing et al. | |
| 6,755,391 B2 | 6/2004 | Newton et al. | |
| 7,296,782 B2 | 11/2007 | Enerson et al. | |
| 7,306,566 B2 | 12/2007 | Raybuck | |
| 7,470,254 B2 | 12/2008 | Basta et al. | |
| 7,666,170 B2 | 2/2010 | Guala | |
| 2003/0066978 A1 | 4/2003 | Enerson | |
| 2005/0090805 A1 | 4/2005 | Shaw et al. | |
| 2006/0142735 A1 * | 6/2006 | Whitley | A61M 39/1011 604/537 |
| 2007/0043334 A1 | 2/2007 | Guala | |
| 2007/0218757 A1 | 9/2007 | Guala | |

FOREIGN PATENT DOCUMENTS

| | | |
|---|---|---|
| JP | 07-148271 | 6/1995 |
| JP | 2007-296317 | 11/2007 |
| WO | 98/50106 A1 | 11/1998 |
| WO | WO2005011799 A1 | 2/2005 |
| WO | WO2006013433 A1 | 2/2006 |

OTHER PUBLICATIONS

PCT/ISA/237—Written Opinion of the International Searching Authority dated May 14, 2009, for corresponding PCT International Application No. PCT/IB2009/000126 filed Jan. 23, 2009.

* cited by examiner

VALVE CONNECTOR FOR MEDICAL LINES

CROSS REFERENCE TO RELATED APPLICATIONS

This application is a national stage of PCT International Application No. PCT/IB2009/000126, filed on Jan. 23, 2009, and published in English on Aug. 6, 2009, as WO 2009/095760 A1, which claims priority from Italian Application No. TO2008A000059, filed on Jan. 29, 2008, the entire disclosures of these applications are incorporated herein by reference.

FIELD OF THE INVENTION

The present invention relates in general to connectors for medical lines, for example for haemodialysis.

More in particular, the invention relates to a valve connector of the type comprising a tubular body having a male inlet fitting with external luer cone, which can be coupled axially by friction within a female fitting with internal luer cone that is to be connected to a first section of the line (for example, a tubing connected to a patient undergoing dialysis). The tubular body has an outlet fitting designed to be connected to a second section of the line (for example, the tubing of a dialyser), and valve means for controlling the passage of flow between the inlet and outlet fittings.

STATE OF THE PRIOR ART

A valve connector of the above sort is described and illustrated in the European patent application No. EP-1747796A1 filed in the name of the present applicant. In said connector, the male inlet fitting of the tubular body comprises an internally threaded external tubular element to be engaged by screwing to the female fitting, and an internal tubular element that can be displaced axially with respect to the tubular body. The valve means are constituted by a transverse diaphragm of a hollow body made of elastic material, equipped with a pre-cut that can be opened elastically by said internal tubular element when this is moved, via the female fitting, from a retracted position of closing to an advanced position of opening of the passage of flow through the tubular body in such a way as to open the communication between the two sections of the medical line. Set between the tubular body and the internal tubular element of the inlet fitting are slidable sealing means, and elastic means are moreover provided that tend to keep the internal tubular element in the retracted closing position, in which the communication between the two sections of the line is interrupted.

In the valve connector according to the document No. EP-1747796, the externally threaded tubular element of the male inlet fitting is fixed with respect to the tubular body and is in fact formed integrally therewith. Opening of the passage of flow through the valve connector is obtained following upon axial engagement of the female fitting with internal luer cone on the male inlet fitting with external luer cone as a result of screwing of the female fitting with respect to the internally threaded external tubular element of the male inlet fitting. Screwing causes axial displacement of the internal tubular element of the male inlet fitting in the direction of the outlet fitting, through the pre-cut diaphragm of the elastic body of the valve means, and consequent opening of the passage of flow.

In the eventuality where, during use of the connector, there accidentally occurs unscrewing between the female fitting and the male inlet fitting of the tubular body, the section of the medical line connected to said female fitting (which, as has been said, in the case of a haemodialysis line, is the section connected to the patient) is subject to the risk of uncontrolled opening. In fact, in this eventuality, whilst the communication between the inlet fitting and the outlet fitting of the tubular body is interrupted as a result of the closing of the valve means following upon return of the internal tubular element of the inlet fitting into the retracted position, the female fitting can disengage completely from the male inlet fitting of the tubular body, thus freeing the flow towards the outside of the corresponding first section of the medical line, with the dramatic consequences that can result therefrom.

SUMMARY OF THE INVENTION

The present invention represents an improvement of the one according to the document No. EP-1747796A1 and has the object of overcoming the drawbacks described above in the case of accidental unscrewing of the female fitting from the male inlet fitting of the tubular body.

According to the invention, the above object is achieved thanks to the fact that the internally threaded external tubular element of the male inlet fitting of the tubular body is free to turn with respect to the internal tubular element, and to the fact that the rotatable external tubular element and the internal tubular element are configured in such a way that, when the external luer cone is axially coupled within the internal luer cone of the female fitting, screwed engagement between the rotatable external tubular element and the female fitting is obtained only following upon an initial axial displacement of the female fitting, which produces a consequent axial displacement of the internal tubular element of the male inlet fitting from the position of closing to the advanced position of opening of the passage of flow against the action of the aforesaid elastic means. Furthermore, the configuration is such that, when the rotatable external tubular element of the male inlet fitting is screwed off the female fitting and the elastic means bring the internal tubular element back from the advanced position of opening into the retracted position of closing of the passage of flow, the aforesaid external luer cone remains axially coupled by friction within the internal luer cone of the female fitting.

Thanks to this arrangement, important advantages are obtained.

In the first place, in the case where during use of the connector there occurs an accidental unscrewing between the female fitting and the male inlet fitting of the tubular body, the risk of uncontrolled opening of the section of the line connected to the female fitting (typically the tubing connected to a patient undergoing haemodialysis) is ruled out. In fact, in this eventuality, closing of the passage of flow through the tubular body, resulting from retraction of the internal tubular element of the male inlet fitting, and the continuance of the axial coupling by friction between the internal luer cone of the female fitting and the external luer cone of the male inlet fitting of the tubular body keep said section of the line in a condition of controlled closing.

A further functional advantage lies in the fact that, when the female fitting is engaged by screwing within the rotatable external tubular element of the male inlet fitting of the tubular body, following upon initial axial displacement of the female fitting, the passage of flow through the valve connector is already open. Subsequent screwing between the rotatable external tubular element of the male inlet fitting and the female fitting produces a further displacement of overtravel of the internal tubular element beyond the aforesaid advanced position of opening of the passage of flow so that the flowrate of the fluid that flows through the connector is the same during the entire step of connection between the male fitting of the tubular body and the female fitting.

Furthermore, the voluntary operation of coupling or uncoupling between the female fitting and the tubular body is facilitated by the rotation of the external tubular element of the male fitting of the tubular body, which prevents any torsion of one and/or other section of the medical line to which the connector is associated in use.

BRIEF DESCRIPTIONS OF THE DRAWINGS

The invention will now be described in detail with reference to the annexed drawings, which are provided purely by way of non-limiting example and in which.

DETAILED DESCRIPTION OF THE INVENTION

Figure 1:
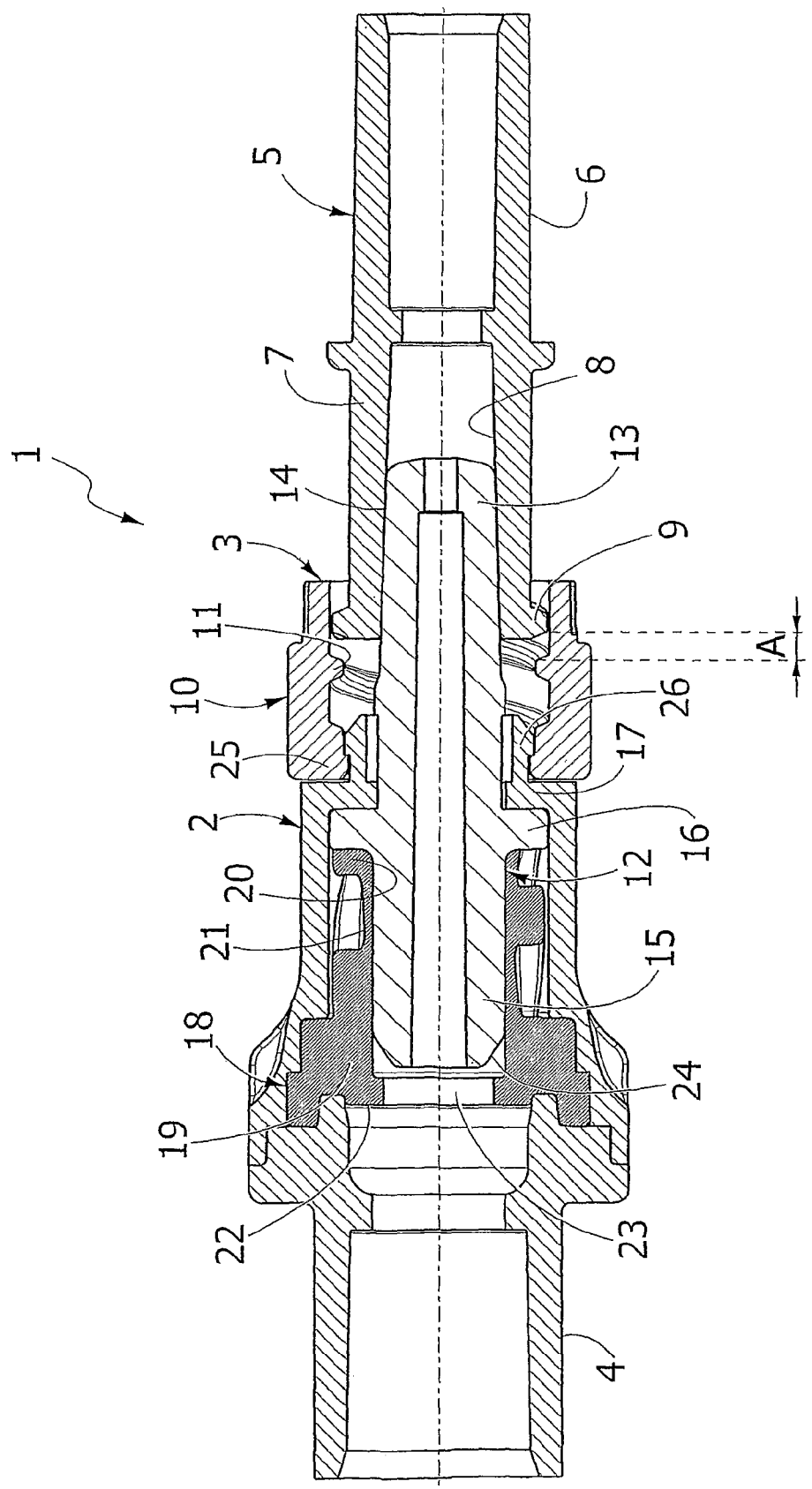
FIG. 1 is a schematic view in longitudinal section of a valve connector according to the invention, represented in the deactivated condition, i.e., where it is closed to the flow of fluid.

With initial reference to FIG. 1, designated as a whole by 1 is a valve connector according to the invention, basically comprising a tubular body 2 provided coaxially at its opposite ends with an inlet fitting 3 and an outlet fitting 4, and a tubular fitting 5. The components listed above of the medical connector 1 can all be made of moulded plastic material.

The tubular fitting 5 has a portion 6 designed to be connected to a first section of a medical line (for example, the tubing connected to a patient undergoing haemodialysis), and a second portion designated by 7, which can be coupled, in the way clarified in what follows, to the inlet fitting 3 of the tubular body 2.

The outlet fitting 4 of the tubular body 2 can in turn be connected to a second section of the medical line (for example, to the tubing of a dialyser).

The portion 7 of the tubular fitting 5 is shaped like a female luer-lock: it has, in a generally conventional way, an internal luer cone 8 and an external end thread 9.

The inlet fitting 3 of the tubular body 2 is of the male luer-lock type, comprising an external tubular element 10 formed with an internal thread 11 complementary to the thread 9 of the female tubular fitting 5, and an internal tubular element 12. Said internal tubular element 12 is mounted axially slidable, with respect to the tubular body 2, between a retracted position, represented in FIG. 1, and an advanced position in the direction of the outlet fitting 4, represented in FIG. 2, passing through the partially advanced position illustrated in FIG. 3.

The internal tubular element 12 has a portion 13 projecting on the outside of the tubular body 2, through, and for a substantial stretch beyond, the internally threaded element 10 shaped like an external luer cone 14, complementary to the internal luer cone 8 of the female tubular fitting 5. Said internal tubular element 12 moreover has an axially internal portion 15 radiused to the axially external portion 13 through an annular flange 16, for example with a polygonal or star shape, coupled in a slidable but non-rotatable way to corresponding internal longitudinal grooves of the body 2 (not visible in the drawings). The flange 16, in the retracted position illustrated in FIG. 1, rests against an internal annular arrest collar 17 of the tubular body 2, and said position is maintained thanks to the action of a hollow element made of elastic material 18 that is interposed substantially in a fluid-tight way within the tubular body 2, between the inlet fitting 3 and the outlet fitting 4 thereof.

This element made of elastic material 18 performs substantially three functions: a first function, as has been said, of elastic thrust of the internal tubular element 12 towards the retracted position; a second function of slidable seal of the portion 15 of the tubular element 12; and a third function consisting in defining a valved passage of flow between the inlet fitting 3 and the outlet fitting 4 of the tubular body 2.

In the embodiment described, the hollow element made of elastic material 18 has, at one end, an enlarged part 19 blocked between the tubular body and the outlet fitting 4 and formed internally with one or more integral seal rings (not visible) in sliding contact with the external surface of the portion 15 of the internal tubular element 12, and an opposite end 20 resting against the annular flange 16 of the internal tubular element 12. An intermediate part 21 of the element 18 has a wall elastically more compliant in an axial direction, conveniently shaped with alternating helical ribbings and grooves, for example, in the way described in detail in the already cited document No. EP-1747796A1.

Furthermore, the elastic tubular body 18 has, in a position corresponding to its end facing the outlet fitting 4, a transverse diaphragm 22 formed with a central cut 23 that is normally kept hermetically closed as a result of an appropriate radial pre-loading between the enlarged part 19 and the tubular body 2.

The free end of the portion 15 of the internal tubular element 12, designated by 24, has a chamfered configuration provided for co-operating, in the way clarified in what follows, with the transverse diaphragm 22 and the corresponding cut 23 of the hollow elastic element 18.

According to the primary characteristic of the invention, the external tubular element 10 with the internal thread 11 of the inlet fitting 3 is constituted by a ring nut that is free to turn on the tubular body 2. Said rotatable ring nut 10 has a rotatably engaged attachment part 25, for example, following upon an axial snap-action coupling, on an axial appendage 26 of the tubular body 2.

According to a further peculiar characteristic of the invention, said rotatable ring nut 10 with the corresponding internal thread 11 and the projecting portion 13 of the internal tubular element 12 formed with the external luer cone 14 are configured in such a way that, when said external luer cone 14 is axially coupled within the internal luer cone 8 of the female fitting 5, screwed engagement between the internal thread 11 of the rotatable ring nut 10 and the external thread 9 of the female fitting 5 is obtained only after engagement by friction between the cones 14 and 8, and following upon an initial axial displacement of the female fitting 5 that produces a consequent axial displacement of the internal tubular element 12 in the direction of the outlet fitting 4, i.e., from the position of closing to the advanced position of opening of the passage of flow through the valve connector 1, compressing the axially more compliant portion 21 of the elastic element 18. The arrangement is moreover such that, when the rotatable ring nut 10 is screwed off the female fitting 5 and consequently the internal tubular element 12 returns into the retracted position for closing the passage through the connector 1 as a result of the elastic return of the portion 21 of the body 18, the cones 14 and 8 remain axially coupled to one another by friction and can be separated from one another only following upon a positive action tending to move them away from one another.

The foregoing will now be explained in greater detail with reference to operation of the valve connector.

In the absence of coupling between the female fitting 5 and the tubular body 2, the internal tubular element 12 is kept by the hollow elastic element 18 in the retracted position represented in FIG. 1. In said condition, the end 24 of the internal tubular element 12 is axially retracted with respect to the transverse diaphragm 22 of the hollow elastic element 18 so that the cut 23 remains hermetically closed and the passage of flow between the inlet fitting 3 and the outlet fitting 4 is interrupted.

When the female tubular fitting 5 is coupled to the tubular body 2, initially the luer cones 8 and 13 are axially engaged to one another by friction, in the way represented in FIG. 1.

Figure 3:
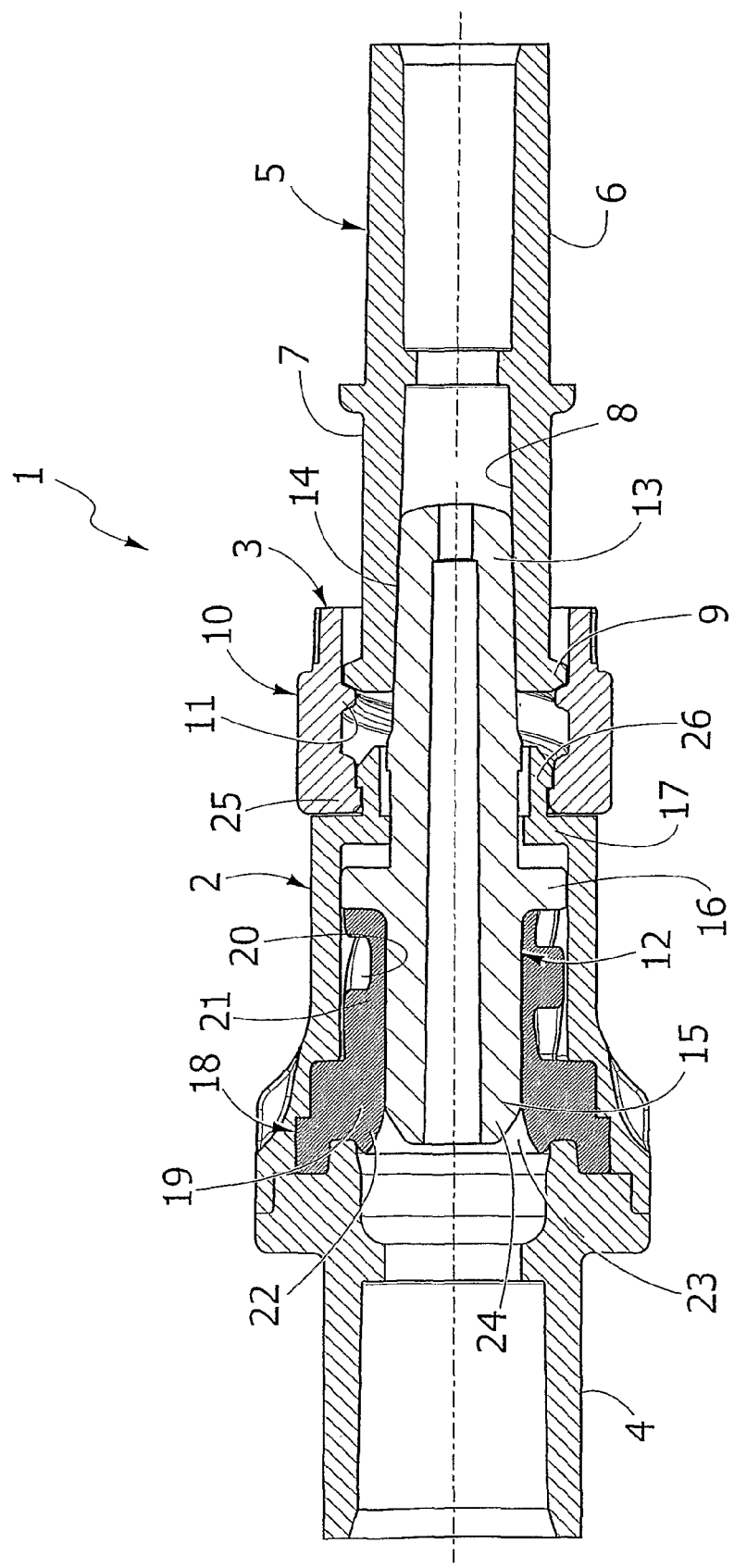
FIG. 3 is a view similar to those of FIGS. 1 and 2, which shows the valve connector in an intermediate condition between the deactivated condition illustrated in FIG. 1 and the activated condition of FIG. 2.

At the end of said axial coupling, between the external thread 9 of the female fitting 5 and start of the internal thread 11 of the rotatable ring nut 10 there remains an axial distance between them, designated by A in FIG. 1, which prevents their mutual engagement and screwing as long as the female fitting 5 and the tubular body 2 are not pushed axially towards one another so as to move the internal tubular element 12 from the retracted position of FIG. 1 into the partially advanced position represented in FIG. 3, where fitting between the threads 9 and 11 is made possible. As is illustrated in FIG. 3, in this condition the end 24 of the internal tubular element 12 has already interacted with the transverse diaphragm 22 of the hollow elastic element 18, expanding elastically and traversing the cut 23 so as to form an initial opening for flow of the fluid through the connector 1.

Figure 2:
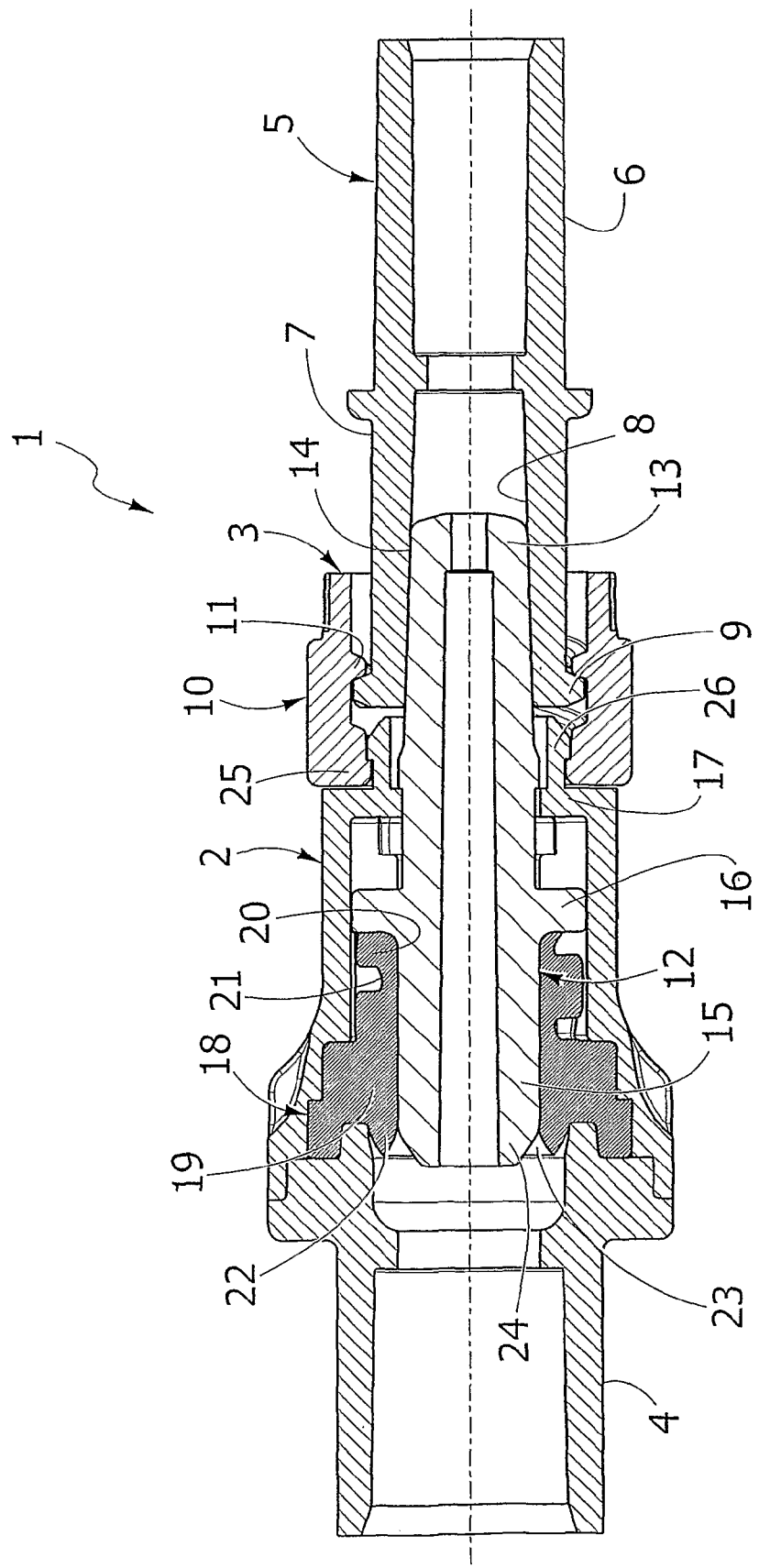
FIG. 2 is a view similar to that of FIG. 1, which shows the valve connector in the activated condition, i.e., where it is open to the flow of fluid.

Starting from said position, a manual rotation of screwing imparted on the rotatable ring nut 10 produces screwing between the threads 9 and 11 and consequently further advance of the female fitting 5 and of the internal tubular element 12 in the direction of the outlet fitting 4 up to the final condition represented in FIG. 2. In said condition, the passage of flow through the connector 1, already opened previously, continues to remain open as a result of the further displacement of overtravel of the end 24 of the internal tubular element 12 through the cut 23 of the diaphragm 22 of the hollow elastic element 18.

The manoeuvre of disengagement between the female tubular fitting 5 and the tubular body 2 obviously involves unscrewing of the rotatable ring nut 10 to obtain disengagement between the threads 9 and 11 and consequent return of the internal tubular element 12 from the condition of FIG. 2 to that of FIG. 1 as a result of the thrust exerted by the hollow elastic element 18, which causes consequent re-closing of the cut 23 and hence of the passage of flow through the connector 1. At the end of said step, to separate the female fitting 5 physically from the tubular body 2 it is necessary to release further the axial coupling by friction between the cones 8 and 14 so as to obtain separation thereof.

The configuration according to the invention described above, with particular reference to the rotatable ring nut 10, to the axial projection of the portion 13 of the internal tubular element 12, and to the reciprocal arrangement of the threads 9 and 11, not only renders more convenient and secure the operations of coupling and uncoupling between the fitting 5 and the tubular body 2, but also ensures a high degree of safety against risks of any accidental opening of the medical line to which the valve connector 1 is applied, in the eventuality in which the threads 9 and 11, in the condition of use of the connector with the passage of flow open, accidentally unscrew and disengage.

In fact, in such an eventuality, the connector 1 sets itself, following upon accidental or in any case undesired unscrewing of the rotatable ring nut 10, in the condition represented in FIG. 1, where retraction of the internal tubular element 12 obtained by the thrust of the hollow elastic element 18 following upon disengagement of the threads 9 and 11 produces closing of the passage of flow as a result of hermetic re-closing of the cut 23 of the diaphragm 22, thus isolating the inlet fitting 3 from the outlet fitting 4. In said condition, the cone 8 of the female fitting 5 remains, however, axially coupled by friction on the cone 14 of the internal tubular element 12 so that the section of the medical line connected to the female fitting 5 is kept closed, in a controlled way, by the valve system of the tubular body 2.

Of course, the details of construction and the embodiments may widely vary with respect to what is described and illustrated herein, without thereby departing from the scope of the present invention, as defined by the ensuing claims.

The invention claimed is:
1. A valve connector for medical lines, comprising:
a female tubular fitting with an internal luer cone;
a tubular body having a male inlet fitting with an external luer cone, an outlet fitting; and a valve means for controlling a passage of flow between said male inlet fitting and said outlet fitting,
said male inlet fitting comprising an external tubular element internally threaded for screwed engagement with said female fitting and an internal tubular element, said internal tubular element formed as a one piece structure with said external luer cone and displaceable axially with respect to said tubular body from a retracted position of closing to an advanced position of opening of said passage of flow, a slidable sealing means of said internal tubular element, and an elastic means tending to keep said internal tubular element in said retracted position of closing,
said internally threaded external tubular element of the male inlet fitting of the tubular body being rotatable with respect to said internal tubular element, said tubular body and said female fitting; and
said internally threaded external tubular element and said internal tubular element are configured in such a way that:
screwed engagement between said internally threaded external tubular element and said female fitting is obtained only following upon an initial axial displacement of said female fitting, which produces a consequent axial displacement of said internal tubular element from the retracted position of closing towards said advanced position of opening of said passage of flow, against an action of said elastic means;
wherein in said advanced position of opening an axial space is located between a first end of said tubular body radially closest to said external tubular element and a second end of said female fitting closest to said external tubular element, the axial space separating the first end of said tubular body and the second end of said female fitting when said external tubular element is in the screwed engagement with said female fitting; and wherein when said internally threaded external tubular element is unscrewed relative to said female fitting and said elastic means brings back said internal tubular element into said retracted position of closing of said passage of flow such that a second axial space separates an external thread of said female fitting and a start of an internal thread of the internally threaded external tubular element such that said external thread of said female fitting and said start of said internal thread are non-contacting relative to each other, said external luer cone remains axially coupled by friction within said internal luer cone and frictionally engaged to said internal luer cone, and the second end of said female fitting is located axially and radially inside said external tubular element and contacting an inner surface of said external tubular element, to prevent uncontrolled separation between the male fitting and the female fitting in the case of the unscrewing being accidental such that a medical line connected to said female fitting is held closed.

2. The valve connector according to claim 1, wherein said valve means, said slidable sealing means, and said elastic means are integrated in a hollow element made of an elastic material interposed axially in a fluid-tight way within said tubular body between said male inlet fitting and said outlet fitting.

3. The valve connector according to claim 1, wherein said external tubular element is located radially outwardly relative to said female fitting and an end of said male inlet fitting closest to said female fitting.

4. The valve connector of claim 1 wherein said internal tubular element is located entirely inside both said tubular body and said female tubular fitting in said retracted position of closing.

5. A method for controlling a flow through a medical line via a valve connector including a female fitting with an internal luer cone and a tubular body having a male inlet fitting with an external luer cone, which can be coupled axially by friction within said female fitting, an outlet fitting, and a valve means for controlling a passage of flow between said inlet fitting and said outlet fitting, wherein said male inlet fitting comprising an internally threaded external tubular element for screwed engagement with said female fitting, and axially coupling the external luer cone of said male inlet fitting with the internal luer cone of the female fitting to provide frictional engagement between said external luer cone and said internal luer cone such that a first axial space remains between said internal luer cone and internal threads of the internally threaded external tubular element;

applying a force to the female fitting to cause the female fitting, including the internal luer cone, and the external luer cone to be displaced in a direction toward the outlet fitting and to contact the female fitting with the internal threads of the internally threaded external tubular element;

wherein the applying the force to the female fitting comprises conveying the force by the internal luer cone to the external luer cone by contact therebetween;

turning the internally threaded external tubular element with respect to an internal tubular element to obtain screwed engagement between said internally threaded external tubular element and said female fitting to displace the internal tubular element of said male inlet fitting axially with respect to said external tubular element from a retracted position of closing to an advanced position of opening of said passage of flow, the displacing of the internal tubular element being against an action of an elastic means tending to keep said internal tubular element in said retracted position, the internal tubular element located within the tubular body, the internal tubular element formed as a one piece structure with the external luer cone;

the displacing the internal tubular element to the advanced position of opening providing a second axial space located between a first end of said tubular body radially closest to said external tubular element and a second end of said female fitting closest to said external tubular element, the second axial space separating the first end of said tubular body and the second end of said female fitting when said external luer cone is axially coupled by friction within said internal luer cone and frictionally engaged to said internal luer cone and when said external tubular element is in the screwed engagement with said female fitting;

turning the internally threaded external tubular element with respect to said internal tubular element to obtain disengagement of said internally threaded external tubular element from said female fitting, said elastic means bringing back said internal tubular element into said retracted position of closing of said passage of flow and providing the first axial space separating said internal luer cone and the internal threads of the internally threaded external tubular element such that an external thread of the female fitting and a start of the internal threads are non-contacting relative to each other, said external luer cone and said internal luer cone remaining axially coupled to one another by friction, and the second end of said female fitting is located axially and radially inside said external tubular element and contacting an inner surface of said external tubular element.

6. The method according to claim 5, wherein the screwed engagement between said internally threaded external tubular element and said female fitting brings about an axial displacement of overtravel of an end of said internal tubular element beyond said advanced position of opening of said passage of flow.

7. The method according to claim 6, wherein said valve means, a slidable sealing means, and said elastic means are provided integrally in a hollow element made of an elastic material set, within said tubular body, between said male inlet fitting and said outlet fitting.

8. The method according to claim 5, wherein said valve means, a slidable sealing means, and said elastic means are provided integrally in a hollow element made of an elastic material set, within said tubular body, between said male inlet fitting and said outlet fitting.

9. A valve connector for medical lines, comprising:
a female tubular fitting with an internal luer cone;
a tubular body, an outlet fitting, and a valve means for controlling a passage of flow between a male inlet fitting and said outlet fitting,
said tubular body engaging an internally threaded external tubular element for screwed engagement with said female fitting,
an internal tubular element formed as a one piece structure with an external luer cone, said internal tubular element received in an interior of said tubular body and displaceable axially with respect to said tubular body from a retracted position of closing to an advanced position of opening of said passage of flow,
a slidable sealing means of said internal tubular element, an elastic means tending to keep said internal tubular element in said retracted position of closing, said external luer cone axially coupled within said internal luer cone of said female fitting such that said external luer cone frictionally engages said internal luer cone;

said internally threaded external tubular element contacting an external surface of said tubular body and said female fitting, said external tubular element avoiding contact with and rotatable with respect to said internal tubular element, said external surface located radially between said external tubular element and said internal tubular element;

said rotatable external tubular element and said internal tubular element are configured in such a way that:

the screwed engagement between said rotatable external tubular element and said female fitting is obtained only following upon an initial axial displacement of said female fitting frictionally engaged with said external luer cone, which produces a consequent axial displacement of said internal tubular element from the retracted position of closing towards said advanced position of opening of said passage of flow, against an action of said elastic means;

wherein an axial space is located between a first end of said tubular body radially closest to said external tubular element and a second end of said female fitting closest to said external tubular element, the space separating the first end of said tubular body and the second end of said female fitting when said external tubular element is in the screwed engagement with said female fitting; and when said rotatable external tubular element is screwed off said female fitting and said elastic means brings back said entire internal tubular element into said retracted position of closing of said passage of flow, said external luer cone remains axially coupled by friction within said internal luer cone and frictionally engaged to said internal luer cone, and the second end of said female fitting is located axially and radially inside said external tubular element and contacting an inner surface of said external tubular element.

10. A valve connector for medical lines, comprising:
a female tubular fitting with an internal luer cone;
a tubular body having a male inlet fitting with an external luer cone, an outlet fitting; and a valve means for controlling a passage of flow between said male inlet fitting and said outlet fitting,
said male inlet fitting comprising an external tubular element internally threaded for screwed engagement with said female fitting and an internal tubular element, an entirety of said internal tubular element displaceable axially with respect to said tubular body from a retracted position of closing to an advanced position of opening of said passage of flow, a slidable sealing means of said internal tubular element, and an elastic means tending to keep said internal tubular element in said retracted position of closing,
said internally threaded external tubular element of the male inlet fitting of the tubular body being rotatable with respect to said internal tubular element, said tubular body and said female fitting; and
said internally threaded external tubular element and said internal tubular element are configured in such a way that:

screwed engagement between said internally threaded external tubular element and said female fitting is obtained only following upon an initial axial displacement of said female fitting, which produces a consequent axial displacement of said internal tubular element from the retracted position of closing towards said advanced position of opening of said passage of flow, against an action of said elastic means; and wherein when said internally threaded external tubular element is unscrewed relative to said female fitting and said elastic means brings back said internal tubular element into said retracted position of closing of said passage of flow such that an axial space separates an external thread of said female fitting and a start of an internal thread of the internally threaded external tubular element such that said external thread of said female fitting and said start of said internal thread are non-contacting relative to each other, said external luer cone remains axially coupled by friction within said internal luer cone and frictionally engaged to said internal luer cone, and a second end of said female fitting is located axially and radially inside said external tubular element and contacting an inner surface of said external tubular element, to prevent uncontrolled separation between the male fitting and the female fitting in the case of the unscrewing being accidental such that a medical line connected to said female fitting is held closed.

11. A method for controlling a flow through a medical line via a valve connector including a female fitting with an internal luer cone and a tubular body having a male inlet fitting with an external luer cone, which can be coupled axially by friction within said female fitting, an outlet fitting, and a valve means for controlling a passage of flow between said inlet fitting and said outlet fitting, wherein said male inlet fitting comprising an internally threaded external tubular element for screwed engagement with said female fitting, and axially coupling the external luer cone of said male inlet fitting with the internal luer cone of the female fitting to provide frictional engagement between said external luer cone and said internal luer cone such that an axial space remains between said internal luer cone and internal threads of the internally threaded external tubular element;

applying a force to the female fitting to cause the female fitting, including the internal luer cone, and the external luer cone to be displaced in a direction toward the outlet fitting and to contact the female fitting with the internal threads of the internally threaded external tubular element;

wherein the applying the force to the female fitting comprises conveying the force by the internal luer cone to the external luer cone by contact therebetween;

turning the internally threaded external tubular element with respect to an internal tubular element to obtain screwed engagement between said internally threaded external tubular element and said female fitting to displace the internal tubular element of said male inlet fitting axially with respect to said external tubular element from a retracted position of closing to an advanced position of opening of said passage of flow, the displacing of the internal tubular element being against an action of an elastic means tending to keep said internal tubular element in said retracted position, the internal tubular element located within the tubular body, the internal tubular element formed as a one piece structure with the external luer cone;

turning the internally threaded external tubular element with respect to said internal tubular element to obtain disengagement of said internally threaded external tubular element from said female fitting, said elastic means bringing back said internal tubular element into said retracted position of closing of said passage of flow and providing the axial space separating said internal luer cone and the internal threads of the internally threaded external tubular element such that an external thread of the female fitting and a start of the internal threads are non-contacting relative to each other, and said external luer cone and said internal luer cone remaining axially coupled to one another by friction, and a second end of said female fitting is located axially and radially inside said external tubular element and contacting an inner surface of said external tubular element.

* * * * *